US008119352B2

(12) United States Patent
Kozma et al.

(10) Patent No.: US 8,119,352 B2
(45) Date of Patent: Feb. 21, 2012

(54) MULTI-STAGE AMPLIFICATION REACTIONS BY CONTROL OF SEQUENCE REPLICATION TIMES

(75) Inventors: Lynn Kozma, Sunol, CA (US); David Douglas Swenson, Ogden, UT (US)

(73) Assignee: Cepheld, Sunnyvale, CA (US)

( * ) Notice: Subject to any disclaimer, the term of this patent is extended or adjusted under 35 U.S.C. 154(b) by 33 days.

(21) Appl. No.: 11/765,240

(22) Filed: Jun. 19, 2007

(65) Prior Publication Data

US 2008/0102495 A1     May 1, 2008

Related U.S. Application Data

(60) Provisional application No. 60/815,365, filed on Jun. 20, 2006.

(51) Int. Cl.
C12Q 1/68     (2006.01)
C12P 19/34     (2006.01)
(52) U.S. Cl. ..................... 435/6.12; 435/91.2
(58) Field of Classification Search .............. None
See application file for complete search history.

(56) References Cited

U.S. PATENT DOCUMENTS

| | | |
|---|---|---|
| 4,230,558 A | 10/1980 | Fulwyler |
| 4,683,195 A | 7/1987 | Mullis et al. |
| 4,683,202 A | 7/1987 | Mullis et al. |
| 4,800,159 A | 1/1989 | Mullis et al. |
| 4,811,218 A | 3/1989 | Hunkapiller et al. |
| 4,883,750 A | 11/1989 | Whitely et al. |
| 4,965,188 A | 10/1990 | Mullis et al. |
| 4,988,617 A | 1/1991 | Landegren et al. |
| 5,126,022 A | 6/1992 | Soane et al. |
| 5,210,015 A | 5/1993 | Gelfand et al. |
| 5,314,809 A | 5/1994 | Erlich et al. |
| 5,399,491 A | 3/1995 | Kacian et al. |
| 5,426,180 A | 6/1995 | Kool |
| 5,427,930 A | 6/1995 | Birkenmeyer et al. |
| 5,434,048 A | 7/1995 | Simon et al. |
| 5,470,723 A | 11/1995 | Walker et al. |
| 5,476,930 A | 12/1995 | Letsinger et al. |
| 5,582,989 A | 12/1996 | Caskey et al. |
| 5,587,128 A | 12/1996 | Wilding et al. |
| 5,589,136 A | 12/1996 | Northrup et al. |
| 5,593,826 A | 1/1997 | Fung et al. |
| 5,646,001 A | 7/1997 | Terstappen et al. |
| 5,648,211 A | 7/1997 | Walker et al. |
| 5,665,582 A | 9/1997 | Kausch |
| 5,674,717 A | 10/1997 | Backus et al. |
| 5,712,124 A | 1/1998 | Walker |
| 5,714,380 A | 2/1998 | Neri et al. |
| 5,786,182 A | 7/1998 | Catanzariti et al. |
| 5,814,491 A | 9/1998 | Vijg et al. |
| 5,814,492 A | 9/1998 | Carrino et al. |
| 5,837,442 A | 11/1998 | Tsang |
| 5,843,761 A | 12/1998 | Barnett et al. |
| 5,849,497 A | 12/1998 | Steinman |
| 5,854,033 A | 12/1998 | Lizardi |
| 5,858,195 A | 1/1999 | Ramsey |
| 5,871,921 A | 2/1999 | Landegren et al. |
| 5,882,856 A | 3/1999 | Shuber |
| 5,965,710 A | 10/1999 | Bodmer et al. |
| 5,972,610 A | 10/1999 | Buchardt et al. |
| 5,985,552 A | 11/1999 | Howell et al. |
| 5,998,224 A | 12/1999 | Rohr et al. |
| 6,001,229 A | 12/1999 | Ramsey |
| 6,010,607 A | 1/2000 | Ramsey |
| 6,033,546 A | 3/2000 | Ramsey |
| 6,033,854 A | 3/2000 | Kurnit et al. |
| 6,048,515 A | 4/2000 | Kresse et al. |
| 6,054,034 A | 4/2000 | Soane et al. |
| 6,057,105 A | 5/2000 | Hoon et al. |
| 6,168,948 B1 | 1/2001 | Anderson et al. |
| 6,174,670 B1 | 1/2001 | Wittwer et al. |
| 6,355,422 B1 | 3/2002 | Liu et al. |
| 6,365,362 B1 | 4/2002 | Terstappen et al. |
| 6,369,893 B1 | 4/2002 | Christel et al. |
| 6,374,684 B1 | 4/2002 | Dority |
| 6,399,952 B1 | 6/2002 | Maher et al. |
| 6,403,037 B1 | 6/2002 | Chang et al. |
| 6,431,476 B1 | 8/2002 | Taylor et al. |

(Continued)

FOREIGN PATENT DOCUMENTS

EP     0263933     4/1988

(Continued)

OTHER PUBLICATIONS

Qiagen one-step RT-PCR kit handbook-fast and efficient one-step RT-PCR (May 2002), available online, www.ebiotrade.com., pp. 1-40.*
Bernard, Philip S. et al.; "Color Multiplexing Hybridization Probes Using the Apolipoprotein E Locus as a Model System for Genotyping"; 1999, *Analytical Biochemistry*, vol. 273, pp. 221-228.
Bustin, S.A.; "Quantification of mRNA using real-time reverse transcription PCR (RT-PCR): trands and problems"; 2002, *Journal of Molecular Endocrinology*, vol. 29, pp. 23-29.
Freeman, Willard M. et al.; "Quantitative RT-PCR: Pitfalls and Potential"; 1999, BioTechniques, vol. 26, No. 1, pp. 112-125.
Hoorfar, J. et al.; "Practical Considerations in Design of Internal Amplification COntrols for Diagnostic PCR Assays"; 2004, *Journal of Clinical Microbiology*, vol. 42, No. 5, pp. 1863-1868.

(Continued)

*Primary Examiner* — Kenneth R. Horlick
*Assistant Examiner* — David Thomas
(74) *Attorney, Agent, or Firm* — Kilpatrick Townsend & Stockton LLP

(57) ABSTRACT

The present invention provides methods and kits for conducting multiplex nucleic acid amplification reactions by controlling target sequence replication times. In one aspect, such control is exerted by selecting different lengths of target polynucleotides for amplification. In another aspect, control is exerted by providing sequence-specific polymerase inhibitors, such as specific blocking oligonucleotides. In accordance with the invention, multiple target polynucleotides can be sequentially amplified in an amplification reaction conducted in different stages, wherein amplification of sequences with longer replication times is permitted in one stage but precluded in other stages by modifying polymerase extension times in the course of the reaction.

6 Claims, 2 Drawing Sheets

U.S. PATENT DOCUMENTS

| | | | |
|---|---|---|---|
| 6,440,725 | B1 | 8/2002 | Pourahmadi et al. |
| 6,472,156 | B1 | 10/2002 | Wittwer et al. |
| 6,605,451 | B1 | 8/2003 | Marmaro et al. |
| 6,613,525 | B2 | 9/2003 | Nelson et al. |
| 6,663,833 | B1 | 12/2003 | Stave et al. |
| 6,783,934 | B1 | 8/2004 | McMillan et al. |
| 6,960,437 | B2 | 11/2005 | Enzelberger et al. |
| 7,101,663 | B2 | 9/2006 | Godfrey et al. |
| 2002/0058258 | A1 | 5/2002 | Witter et al. |
| 2003/0017482 | A1 | 1/2003 | Godfrey et al. |
| 2003/0211483 | A1 | 11/2003 | Schroeder et al. |
| 2004/0146897 | A1 | 7/2004 | Park et al. |
| 2004/0166031 | A1 | 8/2004 | Taylor et al. |
| 2004/0175733 | A1 | 9/2004 | Andersen et al. |
| 2005/0042137 | A1 | 2/2005 | Peterson et al. |
| 2005/0180880 | A1 | 8/2005 | Itoh et al. |
| 2006/0019290 | A1 | 1/2006 | Godfrey et al. |
| 2006/0068418 | A1 | 3/2006 | Godfrey et al. |
| 2006/0068433 | A1 | 3/2006 | Godfrey et al. |
| 2006/0099614 | A1 | 5/2006 | Gill et al. |
| 2006/0115830 | A1 | 6/2006 | Takahashi et al. |
| 2006/0205006 | A1 | 9/2006 | Godfrey et al. |
| 2008/0199867 | A1 | 8/2008 | Godfrey et al. |

FOREIGN PATENT DOCUMENTS

| | | |
|---|---|---|
| EP | 0 519 338 | 12/1992 |
| EP | 0912760 B1 | 12/1997 |
| JP | 04-262799 A | 9/1992 |
| WO | WO 96/39535 | 2/1996 |
| WO | WO 97/46707 A2 | 12/1997 |
| WO | WO 97/46714 A1 | 12/1997 |
| WO | WO 98/08970 A1 | 3/1998 |
| WO | WO 99/13104 | 3/1998 |
| WO | WO 99/19717 A1 | 4/1999 |
| WO | WO 00/72970 | 12/2000 |
| WO | WO 00/73412 | 12/2000 |
| WO | WO 00/73413 | 12/2000 |
| WO | WO 01/45845 | 6/2001 |
| WO | WO 01/57253 | 8/2001 |
| WO | WO 01/84463 | 11/2001 |
| WO | WO 02/18902 | 3/2002 |
| WO | WO 02/24322 A2 | 3/2002 |
| WO | WO 02/052030 | 7/2002 |
| WO | WO 02/070751 A1 | 9/2002 |
| WO | WO 03/055973 | 7/2003 |
| WO | WO 03/072253 A1 | 9/2003 |
| WO | WO 03/072809 | 9/2003 |
| WO | WO 03/077055 A2 | 9/2003 |
| WO | WO 2004/048931 A2 | 6/2004 |
| WO | WO 2006/034215 A2 | 3/2006 |
| WO | WO 2006/047777 A2 | 5/2006 |

OTHER PUBLICATIONS

Jaffe, Richard I. et al.; "Real-Time Identification of *Pseudomonas aeruginosa* Direct From Clinical Samples Using a Rapid Extraction Method and Polymerase Chain Reaction (PCR)"; 2001 *Journal of Clinical Laboratory Analysis*, vol. 15, pp. 131-137.

Leone, Gionata et al.; "Molecular beacon probes combined with amplification by NASBA enable homogeneous, real-time detection of RNA"; 1998, *Nucleic Acids Research*, vol. 26, No. 9, pp. 2150-2155.

Izuta, Shunji et al.; "Chain Termination with Sugar-Modified Nucleotide Analogs in the DNA Polymerase"; 1996, *Nucleosides & Nucleotides*, vol. 15, pp. 683-692.

Koch, Walter H.; "Technology Platforms for Pharmacogenomic Diagnostic Assays"; 2004, *Nature Reviews*, vol. 3, pp. 749-761.

Mackay, Ian M. et al.; "Real-time PCR in virology"; 2002, *Nucleic Acids Research*, vol. 30, No. 6, pp. 1292-1305.

Morrison, Tom B. et al.; "Quantification of Low-Copy Transcripts by Continuous SYBR® Green I Monitoring during Amplification", 1998, *BioTechniques*, vol. 24, No. 6, pp. 954-962.

Qin, Xuan et al.; "Use of Real-Time PCR with Multiple Targets to Identify *Pseudomonas aeruginosa* and other Nonfermenting Gram-Negative Bacilli from Patients with Cystic Fibrosis"; 2003, *Journal of Clinical Microbiology*, vol. 41, No. 9, pp. 4312-4317.

Raja, Siva et al.; "Temperature-controlled Primer Limit for Multiplexing of Rapid, Quantitative Reverse Transcription-PCR Assays: Applicatio to Intraoperative Cancer Diagnostics", 2002, *Clinical Chemistry*, vol. 48, No. 8, pp. 1329-1337.

Schweitzer, Barry et al.; "Combining nucleic acid amplification and detection"; 2001 *Current Opinion in Biotechnology*, vol. 12, pp. 21-27.

Selvey, S. et al.; "β-Actin-an unsuitable internal control for RT-PCR"; 2001, *Molecular and Cellular Probes*, vol. 15, pp. 307-311.

Whitcombe, David et al; "Detection of PCR products using self-probing amplicons and fluorescence"; 1999, *Nature Biotechnology*, vol. 17, pp. 804-807.

ABI PRISM 7700 Sequence Detection System, User Bulletin #2, "Relative Quantitation of Gene Expression," Applied Biosystems (1997/updated Oct. 2001).

ABI PRISM 7700 Sequence Detection System, User Bulletin #5, "Multiplex PCR with TaqMan VIC Probes," Applied Biosystems (1998/updated Jan. 2001).

Abravaya et al., "Molecular beacons as diagnostic tools: technology and applications," 2003, Clinical Chemistry and Laboratory Medicine, 41(4): pp. 468-474.

Battaglia M, et al. "Epithelial tumour cell detection and the unsolved problems of nested RT-PCR: a new sensitive one step method . . . ." Bone Marrow Transplant. 1998;22:693-698.

Bercovich D, et al. "Quantitative ratio of primer pairs and annealing temperature affecting PCR products in duplex amplification." Biotechniques. Oct. 1999;27(4):762-4, 766-8, 770.

Boehringer Mannheim PCR Applications Manual, Boehringer Mannheim Gmbh, Germany, 1995.

Bostick PJ, et al. "Prognostic Significance of Occult Metastases Detected by Sentinel Lymphadenectomy and [RT-PCR] . . ." J Clin Oncol. 1999;17:3238-3244.

Braun D, et al. "Exponential DNA Replication by Laminar Convection." Phys Rev Lett. 2003;91(15):158103.

Brown D,. et al. "Detection of intraoperative tumor cell dissemination in patients with breast cancer by use of reverse transcription and polymerase chain reaction." Surgery. 1995;117(1):96-101.

Buck GA, et al. "Design strategies and performance of custom DNA sequencing primers." Biotechniques. Sep. 1999;27(3):528-36.

Collins C, et al. "Positional cloning of ZNF217 and NABC1: Genes amplified at 20q13.2 and overexpressed in breast carcinoma." Proc. Natl. Acad Sci. USA. 1998;95:8703-8708.

Davison AC & Hinkley DV. "Bootstrap Methods and Their Application." Cambridge, United Kingdom: Cambridge University Press, 1997.

DeLong ER, et al. "Comparing the areas under two or more correlated receiver operating characteristic curves: a nonparametric approach." Biometrics. 1988;44(3):837-845.

Dessau RB, et al. "Coronaviruses in spinal fluid of patients with acute monosymptomatic optic neuritis." Acta Neurol Scand. Aug. 1999;100(2):88-91.

Durmaz R, et al. "Sensitivity of two-stage PCR amplification for detection of Mycobacterium tuberculosis in paraffin-embedded tissues." J Microbiological Methods. 1997;29:69-75.

Efron B & Tibshirani RJ. "An Introduction to the Bootstrap." Boca Raton: Chapman and Hall, 1993: 247-252.

Fitzgerald RC & Triadafilopoulos G. "Recent Developments in the Molecular Characterization of Barretts Esophagus." Dig Dis. 1998;16:63-80.

GenBank Accession No. J03460 (1995). Accessed Oct. 2, 2006.

GenBank Accession No. XM_012777.The NCBI handbook [Internet]. Bethesda (MD): Natl Lib Med (US), 2002, Ch.18. http://www.ncbi.nlm.nih.gov/entrez/query.fcgi?db=Books\n\n.

Gerhard M, et al. "Specific detection of carcinoembryonic antigen-expressing tumor cells in bone marrow aspirates by polymerase chain reaction." J Clin Oncology. Apr. 1994;12(4):725-729.

Gibson UE, et al. "A novel method for real time quantitative RT-PCR." Genome Res. 1996;6:995-1001.

Godfrey TE, et al. "Prognostic Value of Quantitative Reverse Transcription-Polymerase Chain Reaction in Lymph Node-negative Esophageal Cancer Patients." Clin Cancer Res. Dec. 2001;7(12):4041-8.

Godfrey TE, et al. "Quantitative mRNA expression analysis from formalin-fixed, paraffin-embedded tissues using 5 nuclease quantitative RT-PCR." J Mol Diagn. 2000;2:84-91.

Godfrey TE, et al. "Quantitative Reverse Transcription . . . " Proceedings from the 2001 Annual Meeting of the American Association of Cancer Researchers 42. Mar. 1, 2001, # 219.

Harris E, et al. "Typing of dengue viruses in clinical specimens and mosquitoes by single-tube multiplex reverse transcriptase PCR." J Clin Microbiol. Sep. 1998;36(9):2634-9.

Heagerty PJ, et al. "Time-Dependent ROC Curves for Censored Survival Data and a Diagnostic Marker." Biometrics. 2000;56(2):337-845.

Heid CA, et al. "Real time quantitative PCR." Genome Res. 1996;6:986-994.

Krishnan M, et al. "PCR in a Rayleigh-Benard convection cell." Science. 2002;298(5594):793.

Liefers G-J, et al. "Micrometastases and survival in stage II colorectal cancer" [see comments]. N Engl J Med. 1998;339:223-228.

McCallum FS, Maden BE. "Human 18 S ribosomal RNA sequence inferred from DNA sequence . . . " Biochem J. Dec. 15, 1985;232(3):725-33.

Mitas et al., "Qualitative real-time RT-PCR detection of breast cancer micrometastasis using a multigene marker panel," 2001, J. Cancer, 93: pp. 162-171.

Miyake Y, et al. "Quantification of micrometastases in lymph nodes of colorectal cancer using realtime fluorescence polymerase chain reaction." Int J Oncol. 2000;16(2):289-293.

Murphy LC, et al. "Isolation and sequencing of a cDNA clone for a prolactin-inducible protein (PIP). Regulation of PIP gene expression . . . " J Biol Chem. Nov. 5, 1987;262(31):15236-41.

Nakanishi H, et al. "Rapid quantitative detection of carcinoembryonic antigen-expressing free tumor cells in the peritoneal cavity of gastric-cancer patients with real-time RT-PCR on the lightcycler." Int J Cancer. 2000;89:411-417.

Oshima A, et al. "Cloning, sequencing, and expression of cDNA for human beta-glucuronidase." Proc Natl Acad Sci U S A. Feb. 1987;84(3):685-9.

Raja S, et al. "Increased Sensitivity of One-Tube, Quantitative RT-PCR." Bio Techniques. Oct. 2000;29(4):702-706.

Ray et al., "Increasing the denaturation of temperature during the first cycles of amplification reduces allele dropout from single cells to preimplantation genetic diagnosis," 1996, Molecular Human Reproduction, 2(3): pp. 213-218.

Ray PF, Handyside AH. "Increasing the denaturation temperature during the first cycles of amplification reduces allele dropout from . . . " Mol Hum Reprod. Mar. 1996;2(3):213-8.

Roberts CA, et al. "Interpretive disparity among pathologists in breast sentinel lymph node evaluation." Am J Surg. 2003;186(4):324-329.

Shivers SC, et al. "Molecular Staging of Malignant Melanoma: Correlation with Clinical Outcome." JAMA. 1998;280:1410-1415.

Takano T, et al. "Preoperative Diagnosis of Medullary Thyroid Carcinoma by RT-PCR Using RNA Extracted from Leftover Cells within a Needle Used for Fine Needle Aspiration Biopsy." J Clin Endocrinol Metab. Mar. 1999;84(3):951-955.

Tandon AK, et al. "Association of the 323/A3 surface glycoprotein with tumor characteristics and behavior in human breast cancer." Cancer Res. Jun. 1, 1990;50(11):3317-21.

TaqMan One-Step RT-PCR Master Mix Reagents Kit, Protocol, PE Biosystems 1999.

Tassone F, et al. "Elevated Levels of FMR1 mRNA in carrier males: a new mechanism of involvement in the fragile-X syndrome." Am J Hum Genet. 2000;66:6-15.

Troutt AB, et al. "Ligation-anchored PCR: A Simple Amplification Technique with Single-sided Specificity." Proc. Natl. Acad. Sci. USA. 1992;89:98239825.

Viehmann S et al. "Multiplex PCR—a rapid screening method for detection of gene rearrangements in childhood acute lymphoblastic leukemia." Ann Hematol. Apr. 1999;78(4):157-62.

Weiser MR, et al. "Is routine intraoperative frozen-section examination of sentinel lymph nodes in breast cancer worthwhile?" Ann Surg Oncol. 2000; 7:651-655.

Wittwer et al. Real-Time Multiplex PCR Assays, Methods 25(4):430-442 (Dec. 2001).

Wu Dy, et al. "The effect of temperature and oligonucleotide primer length on the specificity and efficiency of amplification . . . " DNA Cell Biol. Apr. 1991;10(3):233-8.

Ylitalo N, et al. "Detection of genital human papillomavirus by single-tube nested PCR and typespecific oligonucleotide hybridization." J Clin Microbiol. Jul. 1995;33(7):1822-8.

* cited by examiner

MULTI-STAGE AMPLIFICATION REACTIONS BY CONTROL OF SEQUENCE REPLICATION TIMES

CROSS-REFERENCES TO RELATED APPLICATIONS

This application claims benefit of U.S. Provisional Application No. 60/815,365, filed Jun. 20, 2006, which is hereby incorporated by reference in its entirety for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The invention relates generally to methods for analyzing a sample for the presence of one or more nucleic acids, and more particularly, to methods for conducting multi-stage nucleic acid amplification reactions, especially polymerase chain reactions (PCRs).

BACKGROUND OF THE INVENTION

Nucleic acid amplification is a crucial component of many techniques used in research, medicine, and industry. Such reactions are used in clinical and biological research, detection and monitoring of infectious diseases, detection of mutations, detection of cancer markers, environmental monitoring, genetic identification, detection of pathogens in biodefense applications, and the like, e.g. Schweitzer et al. *Current Opinion in Biotechnology,* 12:21-27 (2001); Koch, *Nature Reviews Drug Discovery,* 3:749-761 (2004). In particular, polymerase chain reactions (PCRs) have found applications in all of these areas, including applications for viral and bacterial detection, viral load monitoring, detection of rare and/or difficult-to-culture pathogens, rapid detection of bio-terror threats, detection of minimal residual disease in cancer patients, food pathogen testing, blood supply screening, and the like, e.g. Mackay, *Clin. Microbiol. Infect.,* 10:190-212 (2004); Bernard et al. *Clinical Chemistry,* 48:1178-1185 (2002). In regard to PCR, key reasons for such widespread use are its speed and ease of use (typically performed within a few hours using standardized kits and relatively simple and low cost instruments), its sensitivity (often a few tens of copies of a target sequence in a sample can be detected), and its robustness (poor quality samples or preserved samples, such as forensic samples or fixed tissue samples are readily analyzed), Strachan and Read, Human Molecular Genetics 2 (John Wiley & Sons, New York, 1999).

Despite such advances in nucleic acid amplification techniques, there is still a need for further improvements, especially in applications that require rapid identification or quantification of critical markers, such as in infectious disease detection, minimum residual disease detection, bio-defense applications, intraoperative testing for surgical decisions, and the like, e.g. Raja et al. *Clinical Chemistry,* 48:1329-1337 (2002); Yoshioka et al. *Surgery,* 132:34-40 (2002); Qin et al. *J. Clin. Microbiol.,* 41:4312-4317 (2003); Jaffe et al. *J. Clin. Lab. Anal.* 15:131-137 (2001).

In such applications, it is often important to amplify multiple sequences in a closed reaction vessel. These reaction conditions help to minimize false positives from contamination, allow the use of internal or external controls, allow measurement of sequences having widely varying abundances, and the like. To this end, techniques have been developed that allow for sequential amplification of multiple sequences in closed vessels by providing primer sets having widely differing annealing temperatures, e.g. Raja et al. (2002).

Despite the progress noted above, it would be highly useful for applications requiring rapid amplification of multiple sequences if additional methods were available for sequential multiplexing in amplification reactions, particularly if such methods could be combined with existing multiplexing approaches.

BRIEF SUMMARY OF THE INVENTION

The present invention provides methods and kits for conducting multiplex nucleic acid amplification reactions by controlling target sequence replication times. In some embodiments of the invention, the amplification reaction is a polymerase chain reaction (PCR) or a nucleic acid sequence-based amplification (NASBA). In one aspect of the invention, control is exerted by selecting different lengths of target polynucleotides for amplification. In another aspect, control is exerted by providing sequence-specific polymerase inhibitors, such as specific blocking oligonucleotides. In accordance with the invention, multiple target polynucleotides can be sequentially amplified in an amplification reaction conducted in different stages, wherein amplification of sequences with longer replication times is permitted in one stage but precluded in other stages by modifying polymerase extension times in the course of the reaction.

In one aspect, the invention provides a method of controlling a sequentially multiplexed temperature-cycling amplification reaction comprising the following steps: (i) amplifying in a first stage of an amplification reaction at least one first polynucleotide in the presence of a fluorescent indicator in a reaction mixture, the fluorescent indicator being capable of generating an optical signal related to a quantity of an amplicon in the first-stage amplification reaction, and the first-stage amplification reaction having a polymerase extension time with a first value; (ii) monitoring the optical signal of the fluorescent indicator in the first stage; and (iii) changing the polymerase extension time to a second value to initiate a second stage of the amplification reaction whenever the optical signal reaches or exceeds a predetermined level, the second value of the polymerase extension time permitting at least one second polynucleotide to be amplified at a higher rate relative to the rate of at least one first polynucleotide.

In another aspect, the invention provides a method of retarding a replication rate of a selected polynucleotide in a multiplex amplification reaction having a polymerase extension step, such method comprising the following steps: (i) providing for the selected polynucleotide one or more blocker oligonucleotides, each of the one or more blocker oligonucleotides having a sequence complementary to a different portion of the selected polynucleotide or its complement and each such blocker oligonucleotide being present at a concentration such that duplexes form with the selected polynucleotide a predetermined percentage of time during the polymerase extension step; and (ii) extending polynucleotides in the multiplex amplification reaction using a nucleic acid polymerase so that the replication rate of the selected polynucleotide is reduced by blockage of polymerase activity by formation of duplexes between the one or more blocker oligonucleotides and the selected polynucleotide. In some embodiments, the nucleic acid polymerase lacks strand displacement activity.

In another aspect, the invention provides a method of successively amplifying target polynucleotides in a polymerase chain reaction, wherein such method comprises the following steps: (a) providing at least one first target polynucleotide, at least one second target polynucleotide, and at least one third target polynucleotide such that the first target polynucleotide and only the first target polynucleotide has an amplicon melting temperature above a predetermined amplicon melting temperature, the second target polynucleotide and only the second target polynucleotide has a primer melting temperature below a predetermined primer melting temperature, and the third target polynucleotide and only the third target polynucleotide has a replication time above a predetermined polymerase extension time; (b) amplifying in a first-stage reaction the first, second, and third target polynucleotides in the presence of distinct fluorescent indicators for each thereof, each fluorescent indicator being capable of generating a distinct optical signal related to a quantity of the first, second, and third target polynucleotides, respectively, and the first-stage reaction having an amplicon denaturation temperature above the predetermined amplicon melting temperature, a primer annealing temperature below the predetermined primer melting temperature, and a polymerase extension time of a first value that permits the third target polynucleotide to be replicated; (c) monitoring the optical signals of the fluorescent indicators; and (d) successively changing (i) the amplicon melting temperature to a value below that of the predetermined amplicon denaturation temperature, (ii) the primer melting temperature to a value above that of the predetermined primer melting temperature, or (iii) the polymerase extension time to a second value less than the replication time of the third target polynucleotide to initiate a successive reaction stage, whenever the optical signal of a fluorescent indicator reaches or exceeds a predetermined level, so that first, second, and third target polynucleotides are successively amplified.

In still another aspect, the invention includes kits for carrying out the methods of the invention. In one embodiment, a kit of the invention provides components for carrying out a sequentially multiplex amplification of at least two target polynucleotides in a temperature-cycling amplification reaction having an extension step with an extension time, wherein such kit comprises: (i) a first primer pair specific for a first target polynucleotide, the first primer pair defining an amplicon having a first length; and (ii) a second primer pair specific for a second target polynucleotide, the second primer pair defining an amplicon having a second length, wherein the first and second primer pairs are selected such that amplicons having the first and second lengths are produced at a first extension time and such that substantially only the amplicon having the second length is produced at a second extension time. In another embodiment, a kit of the invention provides components for carrying out sequentially multiplex amplification of at least two target polynucleotides in a temperature-cycling amplification reaction having a polymerase extension step, wherein the kit comprises: (i) a first primer pair specific for a first target polynucleotide, the first primer pair defining a first amplicon; (ii) a second primer pair specific for a second target polynucleotide, the second primer pair defining a second amplicon; and (iii) at least one blocking oligonucleotides specific for the first amplicon, the at least one blocking oligonucleotide having a Tm and the at least one blocking oligonucleotide being selected so that whenever the polymerase extension step is carried out at a first temperature greater than the Tm, both the first and second amplicons are produced, and whenever the polymerase extension step is carried out at a second temperature less than the Tm, substantially only the second amplicon is produced.

As disclosed more fully below, kits of the invention may further include additional reagents and materials, such as polymerases, indicators, buffers, disposable reaction cassettes, instructional materials, and the like, for implementing amplification reactions of the invention for a wide range of assays.

DETAILED DESCRIPTION OF THE INVENTION

Definitions

Figure 1A:
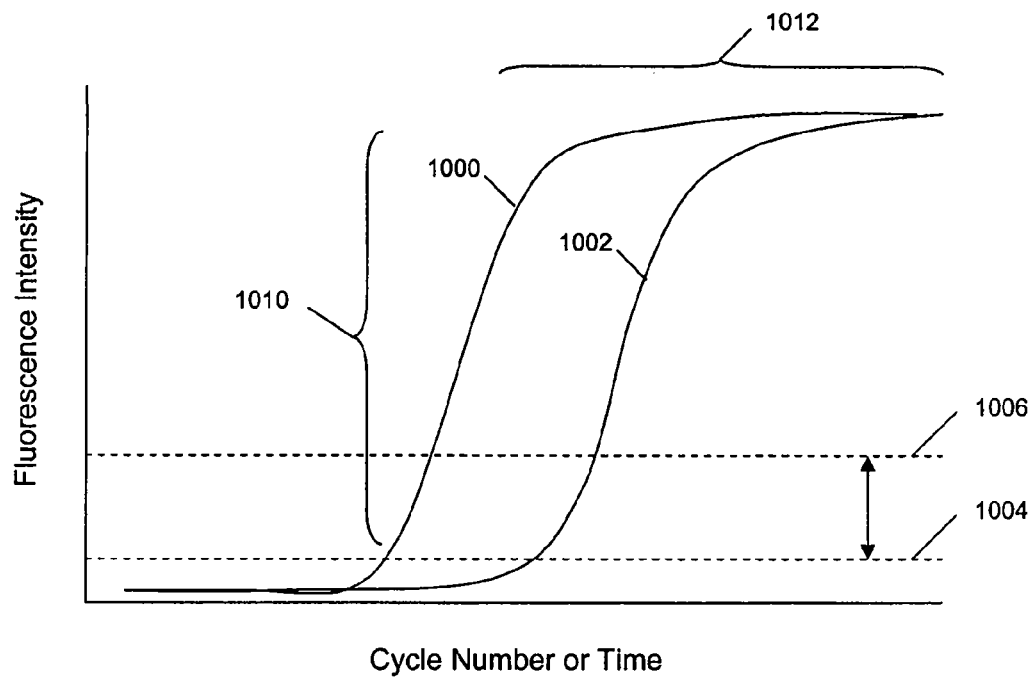
FIGS. 1A-1B illustrate signal v. cycle number (or reaction time) curves for amplification reactions, such as real-time PCRs.

Terms and symbols of nucleic acid chemistry, biochemistry, genetics, and molecular biology used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); Sambrook et al. *Molecular Cloning: A Laboratory Manual*, 2nd Edition (Cold Spring Harbor Laboratory, 1989); and the like.

"Amplicon" as used herein means the product of a polynucleotide amplification reaction. In particular, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, to a target sequence or its complement is required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, ligase chain reactions (LCRs), strand-displacement reactions (SDAs), nucleic acid sequence-based amplification (NASBAs), rolling circle amplifications, and the like, disclosed in the following references that are incorporated herein by reference: Mullis et al U.S. Pat. Nos. 4,683,195; 4,965,188; 4,683,202; 4,800,159 (PCR); Gelfand et al. U.S. Pat. No. 5,210,015 (real-time PCR with TAQMAN™ probes); Wittwer et al. U.S. Pat. No. 6,174,670; Landegren et al. U.S. Pat. No. 4,988,617 ("LCR"); Birkenmeyer et al. U.S. Pat. No. 5,427,930 ("gap-LCR"); Kacian et al. U.S. Pat. No. 5,399,491 ("NASBA"); Walker, U.S. Pat. Nos. 5,648,211; 5,712,124 ("SDA"); Lizardi, U.S. Pat. No. 5,854,033; Aono et al. Japanese Patent Pub. No. JP 4-262799 (rolling circle amplification); and the like. In one aspect, amplicons of the invention are produced in a temperature-cycling amplification reaction that includes repeated steps of denaturing reaction products, usually double stranded DNA, at a first temperature, and annealing primers for polymerase extension at a second temperature. A temperature-cycling amplification reactions of special interest are PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al. *Nucleic Acids Research*, 26:2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Closed" as used in reference to an amplification reaction means that such reaction takes place within a vessel or container or chamber that has no openings through which liquids may pass, in particular, liquids that contain non-sample materials, such as, non-sample biomolecules or organisms, including, but not limited to, nucleic acids, proteins, viruses, bacteria, or the like. In one aspect, a vessel, chamber, or container containing a closed amplification reaction may include a port or vent that is gas permeable but liquid impermeable, for example, a port that permits the venting of air through a filter membrane but not liquids under conventional reaction conditions. Suitable membranes for such ports or vents include woven polyolefin films, such as TYREK™ film (DuPont), or the like.

"Complementary or substantially complementary" as used herein refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably 96%, 97%, 98%, 99%, to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa *Nucleic Acids Res.* 12:203 (1984), incorporated herein by reference.

"Computer-readable product" as used herein means any tangible medium for storing information that can be read by or transmitted into a computer. Computer-readable products include, but are not limited to, magnetic diskettes, magnetic tapes, optical disks, CD-ROMs, punched tape or cards, read-only memory devices, direct access storage devices, gate arrays, electrostatic memory, and any other like medium.

"Duplex" as used herein means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Fluidly closed" as used herein means that, under conventional operating conditions, liquids within a system that comprises one or more vessels, chambers, valves, and/or passages, possibly interconnected and in communication with one another, cannot communicate with the exterior of such a system, and likewise liquids on the exterior of such a system cannot communicate with liquids contained within the interior of the system. In one aspect, conventional operating conditions means that vessels, chambers, valves, and passages of a fluidly closed system are pressurized to an extent less than 100 psi, or in another aspect, to an extent less than 50 psi, or to an extent less than 30 psi.

"Fluorescent indicator" as used herein means a probe that is capable of generating a fluorescent signal in the presence of a product of an amplification reaction (i.e. an "amplification product") such that as product accumulates in the reaction mixture the signal of the fluorescent indicator increases, at least over a predetermined range of concentrations. Fluorescent indicators may be non-specific, such as intercalating dyes that bind to double stranded DNA products, e.g. YO-PRO-1, SYBR green 1, and the like, Ishiguro et al. *Anal. Biochem.* 229:207-213 (1995); Tseng et al. *Anal. Biochem.* 245:207-212 (1997); Morrison et al. *Biotechniques*, 24:954-962 (1998); or such as primers having hairpin structures with a fluorescent molecule held in proximity to a fluorescent quencher until forced apart by primer extension, e.g. Whitecombe et al. *Nature Biotechnology*, 17:804-807 (1999) (AMPLIFLUOR™ primers). Fluorescent indicators also may be target sequence specific, usually comprising a fluorescent molecule in proximity to a fluorescent quencher until an oligonucleotide moiety to which they are attached specifically binds to an amplification product, e.g. Gelfand et al. U.S. Pat. No. 5,210,015 (TAQMAN™); Nazarenko et al. *Nucleic Acids Research*, 25:2516-2521 (1997) ("scorpion probes"); Tyagi et al. *Nature Biotechnology*, 16:49-53 (1998) ("molecular beacons"). Fluorescent indicators may be used in connection with real-time PCR, or they may be used to measure the total amount of reaction product at the completion of a reaction.

"Internal standard" as used herein means a nucleic acid sequence that is amplified in the same amplification reaction as a target polynucleotide in order to permit absolute or relative quantification of the target polynucleotide in a sample. An internal standard may be endogenous or exogenous. That is, an internal standard may occur naturally in the sample, or it may be added to the sample prior to amplification. In one aspect, multiple exogenous internal standard sequences may be added to a reaction mixture in a series of predetermined concentrations to provide a calibration to which a target amplicon may be compared to determine the quantity of its corresponding target polynucleotide in a sample. Selection of the number, sequences, lengths, and other characteristics of exogenous internal standards is a routine design choice for one of ordinary skill in the art. Preferably, endogenous internal standards, also referred to herein as "reference sequences," are sequences natural to a sample that correspond to minimally regulated genes that exhibit a constant and cell cycle-independent level of transcription, e.g. Selvey et al. *Mol. Cell Probes*, 15:307-311 (2001). Exemplary reference sequences include, but are not limited to, sequences from the following genes: GAPDH, β2-microglobulin, 18S ribosomal RNA, and β-actin (see, Selvey et al. 2001).

"Ligation" as used herein means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al. U.S. Pat. No. 4,883,750; Letsinger et al. U.S. Pat. No. 5,476,930; Fung et al. U.S. Pat. No. 5,593,826; Kool, U.S. Pat. No. 5,426,180; Landegren et al. U.S. Pat. No. 5,871,921; Xu and Kool, *Nucleic Acids Research*, 27:875-881 (1999); Higgins et al. *Methods in Enzymology*, 68:50-71 (1979); Engler et al. *The Enzymes*, 15:3-29 (1982); and Namsaraev, U.S. Patent Pub. No. 2004/0110213.

"Microfluidics device" as used herein means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, and a detection system. Microfluidics may further include valves, pumps, and specialized functional coatings on their interior walls, e.g. to prevent adsorption of sample components or reactants; facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 μm to about 0.1 μm. Microfluidics devices typically have volume capacities in the range of from 1 μL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al. U.S. Pat. Nos. 5,126,022 and 6,054,034; Nelson et al, U.S. Pat. No. 6,613,525; Maher et al. U.S. Pat. No. 6,399,952; Ricco et al. Int'l Patent Pub. No. WO 02/24322; Bjornson et al. Int'l Patent Pub. No. WO 99/19717; Wilding et al. U.S. Pat. Nos. 5,587,128; 5,498,392; Sia et al. *Electrophoresis*, 24:3563-3576 (2003); Unger et al. *Science*, 288:113-116 (2000); Enzelberger et al. U.S. Pat. No. 6,960,437.

"Nucleoside" as used herein includes the natural nucleosides, including 2'-deoxy and 2'-hydroxyl forms, e.g. as described in Kornberg and Baker, *DNA Replication*, 2$^{nd}$ Ed. (Freeman, San Francisco, 1992). "Analogs" in reference to nucleosides includes synthetic nucleosides having modified base moieties and/or modified sugar moieties, e.g. described by Scheit, *Nucleotide Analogs* (John Wiley, New York, 1980); Uhlman and Peyman, *Chemical Reviews*, 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (1990); Crooke et al. *Exp. Opin. Ther. Patents*, 6:855-870 (1996); Mesmaeker et al. *Current Opinion in Structural Biology*, 5:343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," as used herein means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al. editors, *PCR: A Practical Approach* and *PCR 2$^{nd}$ Ed.: A Practical Approach* (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," as used herein means a PCR that is preceded by a reverse transcription reaction that converts a target RNA to a complementary single stranded DNA, which is then amplified, e.g. Tecott et al. U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al. U.S. Pat. No. 5,210,015 (TAQMAN); Wittwer et al. U.S. Pat. Nos. 6,174,670 and 6,569,627 (intercalating dyes); Tyagi et al. U.S. Pat. No. 5,925,517 (molecular beacons); each of which are incorporated herein by reference. Detection chemistries for real-time PCR are reviewed in Mackay et al. *Nucleic Acids Research*, 30:1292-1305 (2002), also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. *Anal. Biochem.*, 273:221-228 (1999) (two-color real-time PCR). Usually, distinct sets of primers are employed for each sequence being amplified. Typically, the number of target sequences in a multiplex PCR is in the range of from 2 to 10, or from 2 to 6, or more typically, from 2 to 4.

"Quantitative PCR" as used herein means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al. *Biotechniques*, 26:112-126 (1999); Becker-Andre et al. *Nucleic Acids Research*, 17:9437-9447 (1989); Zimmerman et al. *Biotechniques*, 21:268-279 (1996); Diviacco et al. *Gene*, 122:3013-3020 (1992); Becker-Andre et al. *Nucleic Acids Research*, 17:9437-9446 (1989); and the like.

"Polynucleotide" and "oligonucleotide" are used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al. *Molecular Cloning*, Second Edition (Cold Spring Harbor Laboratory, New York, 1989), and like references.

"Primer" as used herein means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Diefenbach, ed., *PCR Primer: A Laboratory Manual* $2^{nd}$ Edition (Cold Spring Harbor Press, New York, 2003).

"Readout" as used herein means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Tm" or "melting temperature" as used herein means the temperature at which a population of double-stranded nucleic acid molecules becomes half dissociated into single strands. Several equations for calculating the Tm of nucleic acids are well known in the art. For example, a simple estimate of the Tm value may be calculated by the equation. Tm=81.5+0.41 (% G+C), when a nucleic acid is in aqueous solution at 1 M NaCl. Methods for calculating Tm based on more complete models of duplex formation and dissociation are found in Breslauer et al. *Proc. Natl. Acad. Sci.*, 83:3746-3750 (1986); and Wetmur, *Crit. Rev. Biochem. Mol. Biol.*, 26:227-259 (1991).

"Sample" as used herein means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

"Spectrally resolvable" as used in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al., *Flow Cytometry: Instrumentation and Data Analysis*, pages 21-76 (Academic Press, New York, 1985).

"Terminator" as used herein means a nucleotide that cannot be extended by a nucleic acid polymerase. Typically, a terminator can be incorporated into a primer by a polymerase extension reaction, such that the incorporated nucleotide prevents subsequent incorporation of nucleotides to the primer and thereby halts further polymerase-mediated extension. Terminators for enzymatic incorporation are nucleoside triphosphates that lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose nucleosides, for example. Alternatively, a ribofuranose analog can be used in terminators, such as 2',3'-dideoxy-β-D-ribofuranosyl, β-D-arabinofuranosyl, 3'-deoxy-β-D-arabinofuranosyl, 3'-amino-2',3'-dideoxy-β-D-ribofaranosyl, and 2,3'-dideoxy-3'-fluoro-β-D-ribofuranosyl. A variety of terminators are disclosed in the following references: Chidgeavadze et al., *Nucleic Acids Res.*, 12:1671-1686 (1984); Chidgeavadze et al. *FEBS Lett.*, 183:275-278 (1985); Izuta et al. *Nucleosides & Nucleotides,* 15:683-692 (1996); and Krayevsky et al. *Nucleosides & Nucleotides,* 7:613-617 (1988). Nucleotide terminators also include reversible nucleotide terminators, e.g. Metzker et al. *Nucleic Acids Res.,* 22(20):4259 (1994). Oligonucleotides containing terminators may also be chemically synthesized.

Introduction

The invention is directed to methods of sequentially amplifying multiple target polynucleotides in amplification reactions, particularly temperature-cycling amplification reactions, such as PCRs. "Temperature-cycling reaction" means a nucleic amplification reaction that employs repeated cycles of two or more reaction temperatures in the course of amplification. In temperature-cycling reactions using nucleic acid polymerases, such cycles include at least one extension step that takes place at one of the reaction temperatures of each cycle. The extension step has a duration or time during which a nucleic acid polymerase extends one or more primers that have annealed to single strands of either target polynucleotides or amplicons thereof. Temperature-cycling amplification reactions may also be characterized by a frequency at which a cycle is repeated, wherein such frequency is the inverse of the sum of the times or durations of the various steps of the cycle, which, of course, includes at least one extension step. In accordance with the invention, sequential amplification is implemented by controlling one or more target-sensitive parameters during a reaction so that the amplification of specific target polynucleotides is selectively enhanced or inhibited in the course of the reaction. "Target-sensitive parameter" means amplification reaction parameter that affects the rate of amplification of a target polynucleotide. Temperature-sensitive parameters include, but are not limited to, amplicon denaturation temperature, primer annealing temperature, amplicon (or target polynucleotide) replication time, and the like. When one desires to detect or measure multiple target polynucleotides in a sample, the portion of each target that is amplified (and thereby lengths and compositions), primer sets used, and the like, can be selected so that one or more target polynucleotides are preferentially amplified under one set of target-sensitive reaction parameters while other target polynucleotides are preferentially inhibited. Therefore, by sequentially changing such target-sensitive parameters in the course of an amplification reaction, one can sequentially amplify different target sequences; that is, one can carry out a sequentially multiplexed amplification reaction. Such sequential amplification is particularly useful when the target polynucleotides of interest vary widely in concentration. Under such circumstances, the method of the invention can be used to prevent depletion of reactants necessary for the amplification of less abundant species by amplification of abundant species, which is particularly important when reactions are carried out under closed reaction conditions.

The times in an amplification reaction in which target-sensitive parameters are held constant are referred to herein as a "stage" of such a reaction. As used herein, target-sensitive parameters are understood to include the presence or absence of blocking oligonucleotides, as described more fully below. Thus, an amplification reaction of the invention has multiple stages that may be designated as a first stage, second stage, and so on, according to how many successive changes are made in target-sensitive parameters in the course of a reaction.

In one aspect, the invention provides a method for controlling a sequentially multiplexed amplification reaction by controlling the replication time of one or more target polynucleotides. Such control can be implemented by designing a reaction so that a particular amplicon, or group of amplicons, has a greater length than those of other amplicons in the reaction, so that the target-sensitive parameter, polymerase extension time, can be adjusted to permit or prevent the replication of such long amplicons during polymerase extension steps. Such aspect is applicable to any amplification reaction that includes a polymerase extension step, including PCRs, NASBAs, and the like. Target polynucleotides of a reaction can be separated into those having fast polymerase extension times and those having slow polymerase extension times to denote the sequences preferentially amplified or inhibited from amplification. In one aspect, lengths of target polynucleotides to be substantially excluded from amplification at a shortened polymerase extension time (i.e. target polynucleotides having long polymerase extension time) are at least twice those of other target polynucleotides in the same reaction; in still another aspect, such lengths are at least three times those of other target polynucleotides in the same reaction; and in still another aspect, such lengths are at least four time those of other target polynucleotides in the same reaction. In another aspect of the invention, target polynucleotides having short polymerase extension times have lengths in the range of from 50 to 200 nucleotides, and target polynucleotides having long polymerase extension times have lengths in the range of from 200 to 2000 nucleotides, and more preferably in the range of from 400 to 1000 nucleotides. An artisan of ordinary skill is cognizant of other factors besides length that may be important in determining the replication time of an amplicon in a reaction and that in selecting lengths and sequences of amplicons for particular applications some routine empirical experimentation may be employed. In particular, composition and sequence, particularly those that generate secondary structures, such as stems and loops, during an extension step, can also affect replication time. In this aspect of the invention, one of ordinary skill may select amplicons of different lengths by selecting primer pairs specific for target polynucleotides whose sequences are known, using techniques well-known in the art, e.g. as evidenced by the references cited under the definitions of "PCR" and "primer."

In another aspect, control of replication time can be implemented by including non-extendable blocking oligonucleotides in a reaction mixture that specifically anneal to a target polynucleotide to form a duplex that temporarily prevents or inhibits progression of a polymerase. Such blocking oligonucleotides can be included in a reaction mixture at the outset of a reaction so that they become functional in their blocking activity only at reaction temperatures below a certain level. For example, an amplification reaction may have a polymerase extension step that is initially carried out at a first temperature that is greater that the Tm of any blocking oligonucleotide in the reaction so that the production no amplicon is blocked, after which the polymerase extension step is carried out at a second temperature that is less than such Tm so that the production of one or more amplicons of the reaction to which blocking oligonucleotides are capable of specifically annealing is substantially inhibited. In one embodiment, the number, sequence, and length of blocking oligonucleotides are selected so that the rate of production of at least one amplicon is reduced by at least fifty percent, and preferably, by at least eighty percent, at a second temperature less than such Tm. In another aspect, a first temperature is selected that is at least 3° C. above the Tm of any blocking oligonucleotide, and in another aspect, at least 5° C. above the Tm and any blocking oligonucleotide. Likewise, in one aspect, a second temperature is selected that is at least 3° C. below the Tm of any blocking oligonucleotide, and in another aspect, at least 5° C. below the Tm and any blocking oligonucleotide. Alternatively, such blocking oligonucleotides can be added during the course of a reaction to preferentially block or inhibit the amplification of selected target polynucleotides without a change in reaction temperature. Conventional oligonucleotides (that is, comprised of the four natural nucleotides) can be rendered non-extendable by providing them with a 3' terminator. In some embodiments, blocking oligonucleotides are provided that comprise nucleoside analogs and/or non-natural linkages, e.g. peptide nucleic acids (PNAs), oligonucleotide N3'→N5' phosphoramidates, oligo-2'-O-alkylribonucleotides, and the like. In one embodiment, such control is implemented in amplification reactions when polymerases are employed that lack strand displacement activity, such as Taq DNA polymerase. The sequences of blocking oligonucleotides are complementary to those of one or more portions of the amplicon (or its complement) whose replication time is being controlled. The position and length of such complementary portions are selected along with concentration so that during the polymerase extension step a blocking oligonucleotide is duplexed with the portions for a predetermined fraction of the extension step, for example, ten percent, or twenty-five percent, or fifty percent of the time. In one aspect, when blocking oligonucleotides comprise conventional oligonucleotides, in one aspect, they have lengths in the range of from 8 to 30 nucleotides, and more preferably, in the range of from 10 to 20 nucleotides.

In either aspect, amplicons with long replication times, e.g. above a predetermined value for a particular reaction, can be prevented from further replication by shortening in the course of a reaction the duration of the polymerase extension step to a value below the replication time of such amplicons.

In another aspect, the invention provides a method for successively amplifying different target polynucleotides in a PCR by controlling polymerase extension time and the target-sensitive parameters of primer annealing temperature and/or amplicon denaturation temperature. In one embodiment, target polynucleotides are selected that fall into each of three categories: first target polynucleotides such that all first target polynucleotides and only first target polynucleotides have amplicon melting temperatures above a predetermined amplicon denaturation temperature, second target polynucleotides such that all second target polynucleotides and only second target polynucleotides have primer melting temperatures below a predetermined primer melting temperature, and third target polynucleotides such that all third target polynucleotides and only third target polynucleotides have replication times above a predetermined polymerase extension time. First, second, and third target polynucleotides can be markers of tumor cells, bacterial ribosomal sequences, viral genome sequences, or the like. The selection of a predetermined amplicon denaturation temperature, predetermined primer annealing temperature, and predetermined primer extension time are design choices for one of ordinary skill in the art for particular assays and target polynucleotides. The values selected for these predetermined parameters (i.e. target-sensitive parameters) simply serve as boundaries between sets of reaction conditions that either permit or preclude the amplification of certain target polynucleotides. Generally, a wide range of values can be selected depending on the differences in lengths and sequences of the target polynucleotides that one seeks to amplify sequentially.

In one aspect, reaction conditions are selected that initially permit amplification of all of the first, second, and third target polynucleotides. The reaction continues until one of the three target polynucleotides (that is, an amplicon derived therefrom) reaches or exceeds a predetermined level, after which one of the target-sensitive parameters of the reaction is changed to stop further amplification of that target polynucleotide. The reaction continues in a second stage in which only two of the three original sequences undergo further amplification. As above, when one of the two remaining amplicons reaches or exceeds a predetermined level, then the value of its associated target-sensitive parameter is changed to preclude further amplification. The sole remaining target polynucleotide then continues to undergo amplification until it is also detected, or it is confirmed that it is not present, e.g. by observing a signal from an internal or external control, or the like. Selection of the above predetermined signal levels are design choices that depend on the particular assay and are readily determined by routine observation or experimentation. As described more fully below, amplicon concentrations are preferably monitored by a fluorescent signal whose magnitude is proportional to concentration. In these embodiments, the predetermined levels are signal levels (e.g. a fluorescence intensity) that is some factor of the noise level in the detection system, e.g. 1.5 to 10 times the noise level. In an embodiment where at least three stages are carried out, the control of the multi-stage reaction follows a simple tree structure of decisions such that at each branch point (determined by the detection of the next amplicon) one of the target-sensitive parameters is changed to preclude further amplification of the amplicon whose signal just reached or exceeded a predetermined level. Since each of the first, second, and third polynucleotides are selected so that their amplification can be halted by changing one of the target-sensitive parameters, the reaction need be monitored only to determine which of the first, second, or third target polynucleotides reaches or exceeds a predetermined level at the branch point. That observation then determines which of the target-sensitive parameters is changed in the reaction to initiate the next stage.

Thus, with the above association of target polynucleotides with target-sensitive parameters, whenever the first target polynucleotide reaches or exceeds a predetermined level, then the amplicon denaturation temperature is changed to preclude further amplification, so that only the second and third target polynucleotides are amplified in the second stage. Second stage amplification continues until either the second or third target polynucleotide reaches or exceeds a predetermined level. If the second target polynucleotide reaches or exceeds the predetermined level next, then the primer annealing temperature is raised to preclude further amplification of the second target polynucleotide, thereby providing reaction conditions in a third stage so that only the third target polynucleotide is amplified. Likewise, whenever the second target polynucleotide is the initial target polynucleotide to reach or exceed a predetermined level, then the primer annealing temperature is changed to preclude further amplification, so that only the first and third target polynucleotides are amplified in a second stage. Second stage amplification continues until either the first or third target polynucleotide reaches or exceeds a predetermined level. If the first target polynucleotide reaches or exceeds the predetermined level next, then the amplicon denaturation temperature is lowered to preclude further amplification of the first target polynucleotide, thereby providing reaction conditions in a third stage so that only the third target polynucleotide is amplified. Finally, whenever the third target polynucleotide is the initial target polynucleotide to reach or exceed a predetermined level, then the polymerase extension time is changed to preclude further amplification, so that only the first and second target polynucleotides are amplified in a second stage. Second stage amplification continues until either the first or second target polynucleotide reaches or exceeds a predetermined level. If the first target polynucleotide reaches or exceeds the predetermined level next, then the amplicon denaturation temperature is lowered to preclude further amplification of the first target polynucleotide, thereby providing reaction conditions in a third stage so that only the second target polynucleotide is amplified.

In a further aspect, the invention provides methods of conducting reverse transcriptase reactions in series with a multi-stage amplification reaction. In one embodiment, one or more RNA sequences, such as selected mRNAs extracted from a cell or tissue sample, may be amplified as follows: (i) transcribing one or more RNA sequences, for example, in a fluidly closed reaction system, to form at least one complementary single stranded first target polynucleotide and at least one complementary single stranded second target polynucleotide using reverse transcriptase reagents in a reaction mixture; (ii) amplifying in a first-stage amplification reaction at least one first polynucleotide in the presence of a fluorescent indicator in a reaction mixture, the fluorescent indicator being capable of generating an optical signal related to a quantity of an amplicon in the first-stage amplification reaction, and the first-stage amplification reaction having a polymerase extension time with a first value; (iii) monitoring the optical signal of the fluorescent indicator in the first-stage amplification reaction; and (iv) changing the polymerase extension time to a second value to initiate a second-stage amplification reaction whenever the optical signal reaches or exceeds a predetermined level, the second value of the polymerase extension time permitting at least one second polynucleotide to be amplified at a higher rate relative to those of first polynucleotides. The step of transcribing is carried out with a conventional reverse transcriptase reaction, components of which, i.e. reverse transcriptase reagents (a reverse transcriptase, nucleoside triphosphates, reaction buffer), are readily available commercially, e.g. Ambion Inc. (Austin, Tex., USA). In one aspect, the above aspect of the invention is performed in a fluidly closed reaction system.

Control of Sequential Amplifications

In one aspect, the invention provides a method for automatically initiating second and/or subsequent stages of an amplification reaction based on real-time measurements of certain reaction parameters. In one aspect, such automatic initiation of subsequent stages of amplification is under closed-loop control. That is, amplification reactions of the invention are preferably carried out in apparatus that permit parameters associated with multiple classes of amplicons to be monitored. Such parameters include, but are not limited to, fluorescent signals generated by different fluorescent indicators associated with each of at least two (and usually three) different target polynucleotides. Such monitoring includes collecting signals, converting them into digital form, processing the digital information in a processor to determine when and what kind of parameter changes are required to initiate a subsequent stage, and generating control signals to implement such changes. In regard to the present invention, multiple target polynucleotides (or multiple sets of target polynucleotides) are successively amplified under preferential amplification conditions for each such polynucleotide or set of polynucleotides. In one aspect of the invention, reaction conditions are switched in succession to each of the preferential conditions based on real time measurements of the amplicons produced in the on-going reaction, as described in this section.

Figure 1B:
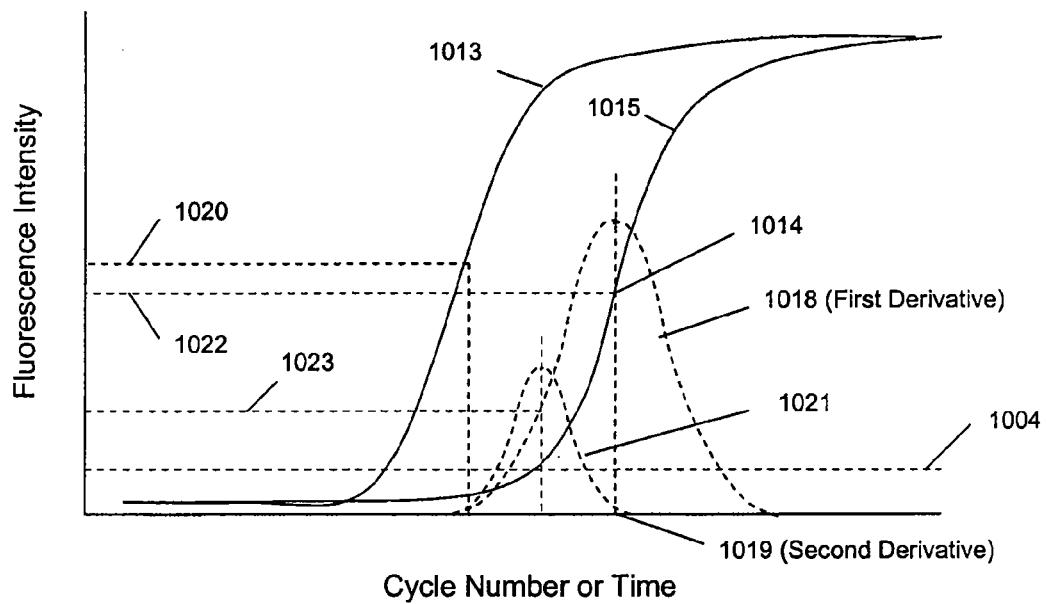

When a first-stage (or prior stage) amplification reaction is under closed-loop control, the value of the reaction parameter at which the subsequent-stage reaction is initiated may be selected in a variety of ways. In one aspect, the value is determined as a function of a baseline signal level, or background noise, or as a characteristic of a function that describes the accumulation of one or more amplicons in the reaction mixture, as illustrated in FIGS. 1A and 1B. In FIG. 1A, curves (1000) and (1002) represent accumulated amplicon of, for example, a reference sequence and target polynucleotide, respectively, as determined by two different fluorescent signals generated by amplicon-specific probes, e.g. molecular beacons having fluorescent dyes that emit fluorescence at distinguishable wavelengths. Such curves are typically sigmoid as illustrated, each having a region of low positive slope below a noise level, or baseline signal, (1004), a log-linear region (1010) of high positive slope, and a plateau region (1012) of low positive slope that corresponds to the stage in the reaction where reactants become exhausted and/or interfering side products accumulate. In one aspect of the invention, a subsequent-stage reaction is initiated when curve (1002) of the target amplicon reaches or exceeds a predetermined level (1006), which may be a function of baseline signal (1004). In another aspect, a subsequent-stage reaction is initiated when both curve (1002) of the target amplicon and curve (1000) of a reference sequence both reach or exceed a predetermined level (1006). Selection of predetermined level (1006) is a routine design choice for one of ordinary skill in the art that may depend on a variety of factors, e.g. the likelihood of sequences closely related to the target being amplified in the first-stage reaction (i.e. lack of specificity in an assay), the quality of the sample and the extent to which it contributes to the baseline signal value, the type of amplification reaction used, the signal detection system employed, and the like. In one aspect, predetermined level (1006) is a multiple of baseline signal value (1004). By way of example, predetermined level (1006) may be selected from a range between 1.5 and 25 times a baseline signal value. In another aspect, predetermined level (1006) is 1.5 times the baseline signal value, or 2 times the baseline signal value, or 3 times the baseline signal value, or 5 times the baseline signal value, or 10 times the baseline signal value. A baseline signal value may be a function, e.g. an average, of fluorescent measurements of a predetermined number of cycles, or for a predetermined time interval, near the beginning of an amplification reaction. The fluorescent measurements may be, or include, measurements of signals from the same channel as that for the fluorescent signal generated by the amplicon being monitored. In one aspect, a baseline signal value is a function of the initial 10, or 25, or 50, or 100 optical signal values measured for at least one amplicon growth curve. In one aspect, such function is an arithmetic average of such initial optical signal values. Preferably, predetermined level (1006) intersects curve (1002) and/or curve (1000) in their respective log-linear regions (1010). Amplicons may be identified and/or measured with a variety of labels that generate optical signals, including but not limited to fluorescent indicators, colorimetric labels, chemiluminescent labels, electrochemiluminescent labels, and the like.

In another aspect, the value of a reaction parameter at which a subsequent-stage reaction is initiated may be determined by a characteristic of a curve describing the relationship of an accumulated amplicon and cycle number or time in an amplification reaction, as illustrated in FIG. 1B (referred to herein as an "amplicon growth curve"). As in FIG. 1A, curve (1013) and curve (1015) describe the accumulation of amplicons corresponding to a reference sequence and a target polynucleotide, respectively. Both curves at each point have positive slopes, however, the magnitude of the slopes changes from early in the reaction to late in the reaction, with the slopes being flat in the beginning, steep in the log-linear region, and flat again in the plateau region. If the derivative is taken of such a curve, a roughly symmetrical function (1018) is produced that has a maximum at time or cycle value (1019). Value (1019) is a root of the first derivative of curve (1015). Value (1019) corresponds to the point (1014) at which the slope of curve (1015) stops increasing and starts decreasing, that is, it is an inflexion point, which is located in approximately the middle of the log-linear region, which makes it an attractive characteristic of curve (1015) for determining a signal value (1022) at which to initiate a subsequent-stage reaction. In another aspect, a second derivative of curve (1015) may be determined to produce another roughly symmetrical function illustrated by curve (1021). The root of curve (1021) provides another candidate characteristic for determining a signal value, e.g. (1023), at which to initiate a subsequent-stage reaction. Determination of signal values corresponding to such characteristics of curves (1015) describing the accumulation of amplicon is disclosed in McMillan et al. U.S. Pat. No. 6,783,934, herein incorporated by reference. As mentioned above, the term "amplicon growth curve" means a curve, such as curves (1000), (1002), (1013), or (1015), that describes the accumulation of amplicon in a reaction mixture as a function of cycle number or time, or as a function of a related parameter, e.g. temperature in a non-temperature regulated amplification reaction, or the like. It is understood that characteristics, such as first or second derivatives, of amplicon growth curves are repeatedly computed during an assay as data making up the curve is collected. It is also understood that because of the real-time nature of the above assays, it may only be possible to determine certain characteristics of an amplicon growth curve retrospectively; thus, such characteristics may not be suitable in every situation for determining when a second-stage amplification reaction should be initiated. Selecting an appropriate characteristic of an amplicon growth curve for determining when to initiate a subsequent-stage amplification reaction is a routine design choice for one of ordinary skill in the art.

Figure 1C:
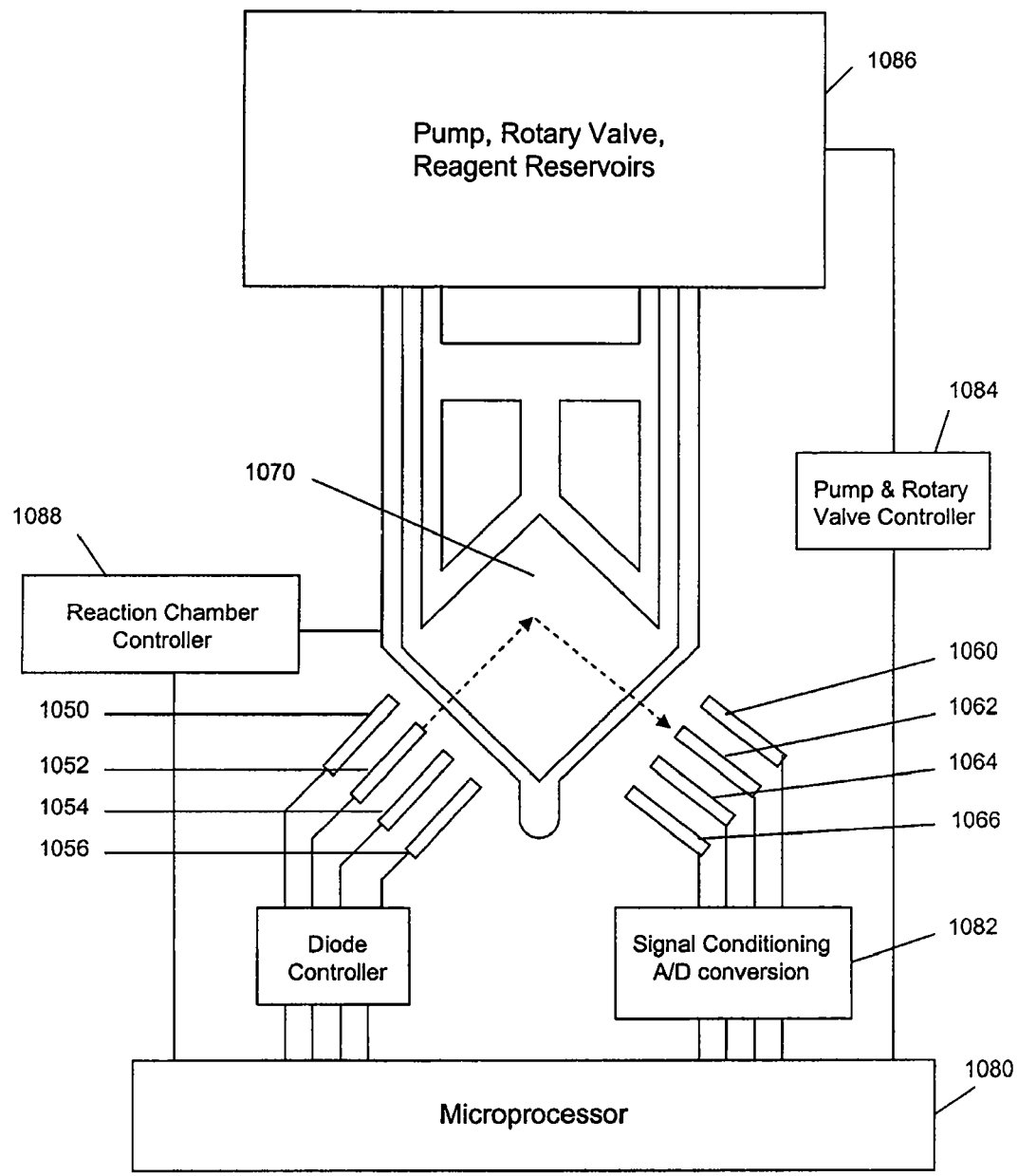
FIG. 1C is a diagram of an apparatus for implementing methods of the invention.

In one aspect of the invention, closed-loop control of initiation of a subsequent-stage reaction is implemented by detecting an optical signal corresponding to a reaction parameter that reaches or exceeds a predetermined value. Preferably, the reaction parameter is concentration of an amplicon, usually the amplicon corresponding to a target polynucleotide. A variety of fluorescent signal generating schemes are available for producing a fluorescent signal in an amplification reaction that is monotonically related to amplicon concentration. such fluorescent signal generating schemes include, but are not limited to, molecular beacons, intercalating dyes, such as SYBR green, taqman probes, AMPLIFLUOR™ primers, "scorpion" primers, and the like, which are disclosed in references cited above. A variety of instrumentation systems may be employed to carry out such closed-loop control based on an optical signal generated by a reaction parameter, such as amplicon concentration. As described more fully below, in one aspect, a multichannel optical detection system disclosed by Christel et al. U.S. Pat. No. 6,369,893 is well-suited for such measurements. A schematic of such a system applicable to the present invention is illustrated in FIG. 1C. Christel et al. provide light sources (1050) through (1056) for illuminating a reaction mixture in reaction chamber (1070). The light sources (1050) through (1056) are preferably light emitting diodes or lasers. Fluorescence excited by light sources (1050) through (1056) is collected by detectors (1060) through (1066), which typically are each operationally associated with a bandpass filter that restricts the wavelength of light that is detected. The excitation beams of light sources (1050) through (1056) may be the same or different. In one aspect, bandpass filters are selected to selectively pass fluorescence emitted by a plurality of spectrally resolvable fluorescent dyes so that each detector (1060) through (1066) collects fluorescence primarily from only one of the plurality of fluorescent dyes. For use with the present invention, one of the light source-detector pairs, for example (1052) and (1062), is allocated to detecting the fluorescent signal from an amplicon corresponding to a target polynucleotide, and one of the light source-detector pairs, for example (1056) and (1066), is allocated to detecting fluorescent signal from an amplicon corresponding to a reference sequence.

Control of all components of the detection system and fluidly closed reaction system (1086) are controlled by microprocessor (1080). Optical signals collected by detectors (1060) through (1066) are processed by conventional optics and converted into electrical signals, which, after conventional pre-amplification and conditioning (1082), are digitized for storage and/or further processing by microprocessor (1080). In one aspect of the invention, microprocessor (1080) is programmed to continuously monitor the value of the signal collected by one of the detectors, such as detector (1062). When the value reaches or exceeds a pre-programmed level, then microprocessor (1080) initiates a subroutine that provides controllers (1084) with a series of commands to actuate components of fluidly closed reaction system (1086) to initiate a second-stage amplification reaction. Microprocessor (1080) also changes and/or regulates the temperature of reaction chamber (1070) through controller (1088). In embodiments employing closed-loop control, microprocessor (1080) may calculate values of characteristics of curves, such as (1013) or (1015) of FIG. 1B, at predetermined intervals so that they may be compared to a predetermined level. When such calculated value reaches or exceeds a predetermined level, then microprocessor (1080) initiates the subroutine to start a subsequent-stage amplification reaction, as described above.

As mentioned above, a computer preferably performs steps of the method of initiating a second-stage reaction, as described above. In one embodiment, a computer comprises a processing unit, memory, I/O device, and associated address/data bus structures for communicating information therebetween. The processing unit may be a conventional microprocessor driven by an appropriate operating system, including RISC and CISC processors, a dedicated microprocessor using embedded firmware, or a customized digital signal processing circuit (DSP), which is dedicated to the specific processing tasks of the method. The memory may be within the microprocessor, i.e. level 1 cache, fast S-RAM, i.e. level 2 cache, D-RAM, or disk, either optical or magnetic. The I/O device may be any device capable of transmitting information between the computer and the user, e.g. a keyboard, mouse, network card, or the like. The address/data bus may be a PCI bus, NU bus, ISA, or any other like bus structure. When the computer performs the method of the invention, the above-described method steps may be embodied in a program stored in or on a computer-readable product. Such computer-readable product may also include programs for graphical user interfaces and programs to change settings on electrophoresis systems or data collection devices. In one aspect, the invention provides algorithms and computer-readable products for controlling the operations described in FIG. 1C in a selected fluidly closed reaction system.

In one aspect of the invention, a computer-readable product comprises a program for execution by a computer to control the performance of a nested amplification reaction in a fluidly closed reaction system. In one embodiment, such a program may comprise instructions for the following: (a) reading values of an optical signal from a first-stage amplification reaction, the optical signal being monotonically related to a concentration of an amplicon in the first-stage amplification reaction, and the values of the optical signal having a most recent value; (b) determining a baseline signal level from the values of the optical signal; (c) computing a predetermined level from the values of the optical signal; (d) comparing the predetermined value with the most recent value of the optical signal; (e) initiating a subsequent-stage amplification reaction whenever the most recent value of the optical signal is equal to or greater than the predetermined level; and (f) repeating steps (d) and (e) until the subsequent-stage reaction is initiated. As used herein, "a most recent value" in reference to an optical signal means the value corresponding to the most recent measurement of an optical signal by a detection system that is monitoring the amplification reaction. In other words, it is the most recent value of an amplicon growth curve as it is generated in the course of an amplification reaction.

By way of example, a fluorescent indicator that can be used with the invention is an AMPLIFLUOR™ hairpin primer, used to generate a fluorescent signal whose intensity is monotonically related to the concentration of an amplicon, e.g. Whitcombe et al. *Nature Biotechnology,* 17:804-808 (1999). Briefly, an AMPLIFLUOR™ hairpin primer has a target-binding portion, which is selected as with a conventional primer, and a hairpin portion at the 5' end of the target-binding portion, which maintains a fluorophore-quencher pair in close proximity whenever the hairpin is present, thereby quenching any fluorescent signal from the fluorophore. During the reverse extension step of the PCR, the duplex region of the hairpin is displaced as the reverse strand is extended through it to the end of the target polynucleotide, thereby moving the quencher away from the proximity of the fluorophore so that a fluorescent signal is generated. As the double stranded DNA product accumulates, the fluorescent signal from the reaction mixture increases. When the intensity of the fluorescent signal reaches or exceeds a predetermined level, e.g. 3 times baseline, a target-sensitive parameter is automatically changed to preclude further amplification of such amplicon.

Since in some applications, a sample may or may not contain a target polynucleotide. Thus, in one aspect, the amplicon of one or more reference sequences, or other internal standard, is monitored for determining whether or when to initiate a subsequent-stage reaction. That is, such an internal standard serves as a positive control and reaction parameter for initiating a subsequent-stage reaction. In another aspect, both amplicons of an internal standard and of a target polynucleotide must reach or exceed predetermined levels, which may be the same or different, in order to initiate a subsequent-stage reaction.

Systems for Implementing Methods of the Invention

Methods of the invention may be implemented by a variety of systems and apparatus based on different engineering approaches for sequestering reagents, moving reagents and reaction products into and out of reactions, controlling temperature, and detecting reaction products. Selection of a system depends on many factors including, but not limited to, availability of samples or specimens, form of samples or specimens, degree of hazard or infectivity posed by samples or specimens, desirability of portability, nature of the amplification reaction employed, and the like. In one aspect, the invention employs disposable reaction cassettes. Such reaction cassettes are designed to perform many different kinds of assays and are typically used with an apparatus that provides ancillary functions, such as temperature control, detection systems, mechanical or electrical power sources to pump, or otherwise move, liquids into and out of cassettes, and the like. Such reaction cassettes can vary widely in shape and scale, from macro-scale, e.g. reaction volumes, reservoir volumes, sample volumes, in 1-10 mL range, to micro-scale, e.g. reaction volumes, reservoir volumes, sample volumes in nanoliter to microliter range. Exemplary systems that may be used with reagent reservoir systems of the invention include fluidly closed reaction systems employing a rotary valve and a piston-type fluid pump under microprocessor control, such as disclosed in Christel et al. U.S. Pat. No. 6,369,893 and Dority, U.S. Pat. No. 6,374,684; and microfluidics devices, such as disclosed in the references cited herein (in particular, those cited under the Definitions section), and further disclosed in Shoji et al, *Appl. Biochem. Biotechnol.*, 41:21-34 (1993) and *J. Micromech. Microeng.*, 4:157-171 (1994); McCormick et al. *Anal. Chem.*, 69:2626-2630 (1997); Cheng et al. *Topics Curr. Chem.*, 194:215-231 (1998); Stave et al. U.S. Pat. No. 6,663,833; Neri et al. U.S. Pat. No. 5,714,380; Northrup et al. U.S. Pat. No. 5,589,136; and the like. Additional reaction cassette system that can be used with the present invention include Petersen et al. U.S. Patent Pub. No. 2005/0042137; and Taylor et al. U.S. Patent Pub. No. 2004/0166031; Catanzariti et al. U.S. Pat. No. 5,786,182; and Itoh et al. U.S. Patent Pub. No. 2005/0180880; which are each herein incorporated by reference. Such systems are capable of fluidly transferring reactants, samples, and reaction products between reservoirs and reaction chambers in a controlled manner. That is, such systems move reactants, samples, reaction products, and the like, in liquid solutions under liquid-moving force in a directed manner. Liquid-moving forces include differential pressure generated by various kinds of pumps or compressed gas reservoirs, electrokinetic pumps, and the like.

In one aspect, methods of the invention may be conveniently implemented by specific designs and methods of operation of rotary valves, reactant and waste reservoirs, and reaction chambers generally disclosed in Dority U.S. Pat. No. 6,374,684. In another aspect, in which real-time monitoring of amplification products is desired, such apparatus is conveniently used with the temperature controller and fluorometer disclosed by Christel et al. U.S. Pat. No. 6,369,893. As will be described more fully below, the apparatus of Christel et al. may further be used to provide closed-loop control of the initiation of a second-stage reaction in the fluidly closed reaction system of Dority.

Internal Standards

Often times it is desirable to compare readouts from different assays, for example, when attempting to determine whether measured expression levels of a target gene in a patient specimen are within normal ranges. In medical applications in particular, it is often desired to compare assay results from a patient sample to those of reference samples. Such comparisons are readily made by determining ratios of a signal associated with the target polynucleotide to a signal associated with a reference sequence from the same sample. This permits values for a target polynucleotide to be compared to those from other samples or specimens. Use and selection of internal standards, and in particular, reference sequences, are well-known to those of ordinary skill in the art, as reflected in the following references that are incorporated by reference: Radonic et al. *Biochem. Biophys. Res. Comm.*, 313:856-862 (2004); Bustin, *J. Mol. Endocrinol.*, 29:23-39 (2002); Hoorfar et al. *J. Clin. Microbiol.*, 42:1863-1868 (2004); and the like. It is understood that the signal or a value associated with a reference sequence may also be a function, for example, an average, of signals or values measured from multiple reference sequences.

In one aspect of the invention, such relative values of target polynucleotides is provided by amplifying both reference sequences and target polynucleotides in a first-stage amplification reaction, amplifying only amplicons of target polynucleotides in a second-stage amplification reaction, and forming a ratios each comprising a signal from an amplicon of a target polynucleotide in the second amplification reaction to a signal from an amplicon of a reference sequence in the first amplification reaction. This aspect of the invention is particularly well-suited for comparing levels of rare, or very low level, target polynucleotides from different samples. In such circumstances, reference sequences are typically present in great excess of the target polynucleotides; consequently, if both sequences were to undergo two stages of amplification, the reference sequence signal may easily overwhelm the target polynucleotide signal, if the respective signals even slightly overlap, as is the case with emission bands of organic fluorescent dyes. Accordingly, in one embodiment of this aspect, a method of measuring relative quantities of a target polynucleotide in multiple samples is provided by carrying out a nested PCR wherein (i) a reference sequence is amplified in a first-stage PCR but not in a second-stage PCR and (ii) relative quantities of a target polynucleotide are determined from ratios of the following two measurements: a fluorescent signal from an amplicon produced in the second-stage PCR from a target polynucleotide, and a fluorescent signal from an amplicon produced in the first-stage PCR from a reference sequence. In a preferred embodiment, both the first-stage and second-stage reactions are real-time PCRs.

The type of internal standard or reference sequence selected depend on the nature of the samples being analyzed. For samples comprising mammalian cells or tissues exemplary references sequences are listed in Table I.

TABLE I

Exemplary Reference Sequences

| Reference Gene | Gene Product Name | NCBI Accession No. |
|---|---|---|
| GAPDH | glyceraldehydes 3-phosphate dehydrogenase | J02642 |
| G6PDH | glucose 6-phosphate dehydrogenase | X03674 |
| HPRT | hypoxanthine-guanine phosphoribosyltransferase | L29382 |
| PBGD | porphobilinogen deaminase | X04808 |
| Alb |  | L00132 |
| Act | β-actin | M10277 |
| Tub | α-tubulin | X01703 |
| TBP | TATA-box binding protein | M55654 |
| L13 | ribosomal protein L13 | X56923 |
| β2M | β2-microglobulin | J00115 |
| PPIA | peptidyl prolyl isomerase A | Y00052 |
| PLA | phospholipase A2 | M86400 |
|  | 18S and 28S ribosomal RNA |  |

Sample or Specimen Preparation

Samples or specimens containing target polynucleotides may come from a wide variety of sources for use with the present invention, including cell cultures, animal or plant tissues, patient biopsies, environmental samples, or the like. Samples are prepared for assays of the invention using conventional techniques, which typically depend on the source from which a sample or specimen is taken.

Samples or specimens are collected so as to minimize the chance of contamination of the sample or specimen by external elements, or the environment by the sample or specimen if it contains hazardous components. Generally, this is carried out by introducing a sample for analysis, e.g., tissue, blood, saliva, etc., directly into a sample collection chamber within a fluidly closed system. Typically, the prevention of cross-contamination of the sample may be accomplished by directly injecting the sample into the sample collection chamber through a sealable opening, e.g., an injection valve, or a septum. Generally, sealable valves are preferred to reduce any potential threat of leakage during or after sample injection. In addition to the foregoing, the sample collection portion of the device may also include reagents and/or treatments for neutralization of infectious agents, stabilization of the specimen or sample, pH adjustments, and the like. Stabilization and pH adjustment treatments may include, e.g., introduction of heparin to prevent clotting of blood samples, addition of buffering agents, addition of protease or nuclease inhibitors, preservatives and the like. Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

Prior to carrying out amplification reactions on a sample, it will often be desirable to perform one or more sample preparation operations upon the sample. Typically, these sample preparation operations will include such manipulations as extraction of intracellular material, e.g., nucleic acids from whole cell samples, viruses and the like. One or more of these various operations may be readily incorporated into the fluidly closed systems contemplated by the present invention.

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like. Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within a sample preparation chamber, a separate accessible chamber, or may be externally introduced.

Physical methods may be used to extract the nucleic acids and denature DNA binding proteins. Wilding et al. U.S. Pat. No. 5,304,487, incorporated herein by reference in its entirety for all purposes, discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g., employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to perform cell lysis/extraction, including, e.g., subjecting cells to ultrasonic agitation, or forcing cells through small apertures, thereby subjecting the cells to high shear stress resulting in rupture.

Following extraction, it will often be desirable to separate the nucleic acids from other elements of the crude extract, e.g., denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the devices of the present invention, and is commercially available from, e.g., Pharmacia and Sigma Chemical (St. Louis, Mo.).

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g., charged groups, affinity binding groups and the like, i.e., poly-T oligonucleotides for mRNA purification. Alternatively, desalting methods may generally take advantage of the high electrophoretic mobility and negative charge of DNA compared to other elements. Electrophoretic methods may also be utilized in the purification of nucleic acids from other cell contaminants and debris. In one example, a separation channel or chamber of the device is fluidly connected to two separate "field" channels or chambers having electrodes, e.g., platinum electrodes, disposed therein. The two field channels are separated from the separation channel using an appropriate barrier or "capture membrane" which allows for passage of current without allowing passage of nucleic acids or other large molecules. The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g., acting as a salt junction). Such barriers may include, e.g., dialysis membranes, dense gels, PEI filters, or other suitable materials. Upon application of an appropriate electric field, the nucleic acids present in the sample will migrate toward the positive electrode and become trapped on the capture membrane. Sample impurities remaining free of the membrane are then washed from the chamber by applying an appropriate fluid flow. Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use. In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

For a number of applications, it may be desirable to extract and separate messenger RNA from cells, cellular debris, and other contaminants. As such, a system of the present invention may, in some cases, include an mRNA purification chamber or channel. In general, such purification takes advantage of the poly-A tails on mRNA. In particular and as noted above, poly-T oligonucleotides may be immobilized within a chamber or channel of the device to serve as affinity ligands for mRNA. Poly-T oligonucleotides may be immobilized upon a solid support incorporated within the chamber or channel, or alternatively, may be immobilized upon the surface(s) of the chamber or channel itself.

In some applications, such as measuring target polynucleotides in rare metastatic cells from a patient's blood, an enrichment step may be carried out prior to conducting an assay, such as by immunomagnetic isolation. Such isolation or enrichment may be carried out using a variety of techniques and materials known in the art, as disclosed in the following representative references that are incorporated by reference: Terstappen et al. U.S. Pat. Nos. 6,365,362, 5,646, 001; Rohr et al. U.S. Pat. No. 5,998,224; Kausch et al. U.S. Pat. No. 5,665,582; Kresse et al. U.S. Pat. No. 6,048,515; Kausch et al. U.S. Pat. No. 5,508,164; Miltenyi et al. U.S. Pat. No. 5,691,208; Molday, U.S. Pat. No. 4,452,773; Kronick, U.S. Pat. No. 4,375,407; Radbruch et al. Chapter 23, in *Methods in Cell Biology*, Vol, 42 (Academic Press, New York, 1994); Uhlen et al. *Advances in Biomagnetic Separation* (Eaton Publishing, Natick, 1994); Safarik et al. *J. Chromatography B*, 722:33-53 (1999); Miltenyi et al. *Cytometry*, 11:231-238 (1990); Nakamura et al. *Biotechnol. Prog.*, 17:1145-1155 (2001); Moreno et al. *Urology*, 58:386-392 (2001); Racila et al. *Proc. Natl. Acad. Sci.*, 95:4589-4594 (1998); Zigeuner et al. *J. Urology*, 169:701-705 (2003); Ghossein et al. *Seminars in Surgical Oncology*, 20:304-311 (2001).

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, north pole, south pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. This magnetic separation characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698, 271, hereby incorporated by reference.

Kits of the Invention

In the commercialization of the methods described herein, certain kits for detection of specific nucleic acids are particularly useful. A test kit typically comprises one or more reagents, such as, without limitation, nucleic acid primers or probes, packaged in a container, such as, without limitation, a vial, tube or bottle, in a package suitable for commercial distribution, such as, without limitation, a box, a sealed pouch, a blister pack and a carton. The package typically contains a label or packaging insert indicating that the packaged reagents can be used in a method for identifying expression or markers indicative of the presence of cancer cells in a lymph node of a patient. As used herein, "packaging materials" includes any article used in the packaging for distribution of reagents in a kit, including without limitation containers, vials, tubes, bottles, pouches, blister packaging, labels, tags, instruction sheets and package inserts. One example of such a kit would include reagents necessary for a one-tube quantitative RT-PCR process. In one example, the kit would include the above-described reagents, including reverse transcriptase, a reverse transcriptase primer, one or more primer pairs, a thermostable DNA polymerase, such as Taq polymerase, and a suitable fluorescent indicator, such as, without limitation, a probe for a fluorescent 5' nuclease assay, a molecular beacon probe, a single dye primer or a fluorescent dye specific to double-stranded DNA, such as ethidium bromide. The primers may be present in quantities that would yield operable reaction concentrations for the amplification reaction to be implemented by a kit. Thermostable DNA polymerases are commercially available from a variety of manufacturers. Additional materials in the kit may include: suitable reaction tubes or vials, a barrier composition, typically a wax bead, optionally including magnesium; reaction mixtures (often concentrated, for example 2×, 5×, 10× or 20×) for the reverse transcriptase and the PCR stages, including necessary buffers and reagents such as dNTPs; nuclease- or RNase-free water; RNase inhibitor; control nucleic acid(s) and/or any additional buffers, compounds, co-factors, ionic constituents, proteins and enzymes, polymers, and the like that may be used in reverse transcriptase and/or PCR stages of quantitative RT-PCR reactions.

Components of a kit are packaged in any manner that is commercially practicable. For example, PCR primers and reverse transcriptase may be packaged individually to facilitate flexibility in configuring the assay, or together to increase ease of use and to reduce contamination. Similarly, buffers, salts and co-factors can be packaged separately or together. The kits also may include reagents and mechanical components suitable for the manual or automated extraction of nucleic acid from a tissue sample. These reagents are known to those skilled in the art and typically are a matter of design choice. For instance, in one embodiment of an automated process, tissue is disrupted ultrasonically in a suitable lysis solution provided in the kit. The resultant lysate solution is then filtered and RNA is bound to RNA-binding magnetic beads also provided in the kit or cartridge. The bead-bound RNA is washed, and the RNA is eluted from the beads and placed into a suitable reverse transcriptase reaction mixture prior to the reverse transcriptase reaction. In automated processes, the choice of reagents and their mode of packaging (for instance in disposable single-use cartridges) typically are dictated by the physical configuration of the robotics and fluidics of the specific RNA extraction system, for example and without limitation, the GENEXPERT® system. International Patent Pub. Nos. WO 04/48931, WO 03/77055, WO 03/72253, WO 03/55973, WO 02/52030, WO 02/18902, WO 01/84463, WO 01157253, WO 01/45845, WO 00/73413, WO 00/73412 and WO 00/72970 provide non-limiting examples of cartridge-based systems and related technology useful in the methods described herein.

The constituents of the kits may be packaged together or separately, and each constituent may be presented in one or more tubes or vials, or in cartridge form, as is appropriate. The constituents, independently or together, may be packaged in any useful state, including without limitation, in a dehydrated, lyophilized, classified or aqueous state. The kits may take the physical form of a cartridge for use in automated processes, having two or more compartments including the above-described reagents. Suitable cartridges are disclosed for example in U.S. Pat. Nos. 6,440,725, 6,431,476, 6,403,037 and 6,374,684. As mentioned above, PCR-based technologies may be used to quantify mRNA levels in a given tissue sample. Other sequence-specific nucleic acid quantification methods may be more or less suited, so long as differences in Tm between reagents can be effectively exploited to balance the multiplexed reaction. As is understood in the field of the present invention, many variations to the standard multiplexed "PCR" reaction are known, and many exist in which differences in amplicon denaturation temperatures and/or differences in primer anneal temperatures can be exploited with the goal of balancing the multiplex reaction.

Example

In this example, three polynucleotide markers are detected by selecting each so that its amplification can be terminated by changing an associated target-sensitive parameter in the course of a multi-stage PCR. The specific parameters associated with each marker are shown in Table 2. The multi-stage reaction is performed on a SMARTCYCLER™ (Cepheid, Sunnyvale, Calif.) and analyzed with SMARTCYCLER™ software. Marker 1 is subject to denaturation temperature dependence. It has a high Tm amplicon and high Tm primers, but is relatively short (e.g. 100±20 bp). Marker 2 is subject to anneal temperature dependence. It has a lower Tm amplicon and lower Tm primers, but is relatively short (e.g. 100±20 bp). Marker 3 is subject to extension time dependence. It has a lower Tm amplicon and high Tm primers, but is relatively long (e.g. ≧250 bp).

TABLE 2

| Marker | Amplicon Tm | Primer Tm | Extension Time |
|---|---|---|---|
| 1 | 89 | 71 | 6 sec |
| 2 | 78 | 63 | 6 sec |
| 3 | 79 | 70 | 15 sec |

Cycling Protocols for each of the different stages of the reaction are shown below in Table 3. Following the initial template denaturation hold step, the first amplification cycling protocol would be set to amplify all 3 markers. All 3 dye channels would be actively monitored for signal generation (Ct). Specification within the software would dictate which subsequent cycling stage would be switched to depending upon which channel is detected first.

TABLE 3

| Stage | Denature | Anneal | Extend | Monitor | Comments |
|---|---|---|---|---|---|
| 1 | 94 C. 2" | 60 C. 4" | 68 C. 15" | 1, 2, 3 | Amplifies all 3 markers |
| 2 | 94 C. 2" | | 68 C. 15" | 1, 3 | Amplifies markers 1 & 3; terminates marker 2. |
| 3 | 85 C. 2" | 60 C. 4" | 68 C. 15" | 2, 3 | Amplifies markers 2 & 3; terminates marker 1. |
| 4 | 94 C. 2" | 60 C. 4" | 68 C. 6" | 1, 2 | Amplifies markers 1 & 2; terminates marker 3. |
| 5 | 94 C. 2" | | 68 C. 6" | | Amplifies marker 1; terminates markers 2 & 3. |
| 6 | 85 C. 2" | | 68 C. 15" | | Amplifies marker 3; terminates markers 1 & 2. |
| 7 | 85 C. 2" | 60 C. 4" | 68 C. 6" | | Amplifies marker 2; terminates markers 1 & 3. |

In the example given above, stage 1 is the general cycling protocol and all 3 markers can be amplified with equal efficiency. Signal generation is a function of template input amount. If the software monitors all 3 dye channels for a signal (Ct), the software can automatically switch to an alternate (and appropriate) stage. For example, if marker 1 generates a Ct first, the software would switch automatically to stage 3 in which marker 1 amplification is terminated allowing markers 2 and 3 to continue amplification. These 2 markers are monitored in stage 3. If marker 2 is detected, the switch is made to stage 6. If, however, marker 3 is detected instead, the switch would be to stage 7.

The reason for incorporating such a scheme into a RT-PCR reaction design strategy is so that the "swamping out" of lower abundance targets is minimized or avoided. This would increase the linear dynamic range of 3 separate markers in a multiplex RT-PCR reaction. Without the ability to terminate selectively and in real time, the most abundant target in a sample would limit the detection ability of the other 2 markers to a range of certainly less than 5 Ct difference and likely lower than that if the remaining 2 markers were not of equal abundance. In cases where you do not have a priori knowledge of the relative abundance of the 3 markers in the full range of expected samples and need to know the relative abundance of those 3 markers to make a clinically relevant call, this scheme would provide the necessary linear dynamic range to accomplish this.

It is understood that the examples and embodiments described herein are for illustrative purposes only and that various modifications or changes in light thereof will be suggested to persons of skill in the art and are to be included within the spirit and purview of this application and scope of the appended claims. All publications, patents, patent applications, and sequence accession numbers cited herein are hereby incorporated by reference in their entirety for all purposes.

What is claimed is:

1. A method of amplifying target polynucleotides, the method comprising the steps of:

providing a first target polynucleotide, a second target polynucleotide, and a third target polynucleotide, such that the first target polynucleotide and only the first target polynucleotide has an amplicon melting temperature above a predetermined amplicon melting temperature, the second target polynucleotide and only the second target polynucleotide has a primer annealing temperature below a predetermined primer annealing temperature, and the third target polynucleotide and only the third target polynucleotide has a replication time above a predetermined polymerase extension time;

amplifying in a first stage reaction using a nucleic acid polymerase the first, second, and third target polynucleotides in the presence of three distinct fluorescent indicators, each fluorescent indicator generating a distinct optical signal indicating quantity of amplification products of the first, second, and third target polynucleotides, respectively, and the first-stage reaction having an amplicon denaturation temperature above the predetermined amplicon melting temperature, a primer annealing temperature below the predetermined primer annealing temperature, and a polymerase extension time above the predetermined polymerase extension time, such that each of the first, second, and third target polynucleotides is amplified in the first stage reaction;

monitoring the optical signals of the fluorescent indicators; and initiating a second stage reaction by changing the reaction condition of the first stage reaction as follows and in any order: (1) whenever the optical signal of the fluorescent indicator indicating the quantity of the amplification product of the first target polynucleotide reaches or exceeds a predetermined level, reducing the amplicon denaturation temperature of the reaction to below the predetermined amplicon melting temperature but above each of the amplicon melting temperatures of the second and third target polynucleotides, thereby terminating amplification of the first target polynucleotide, (2) whenever the optical signal of the fluorescent indicator indicating the quantity of the amplification product of the second target polynucleotide reaches or exceeds a predetermined level, increasing the primer annealing temperature of the reaction to above the predetermined primer annealing temperature but below each of the primer annealing temperatures of the first and third target polynucleotides, thereby terminating amplification of the second target polynucleotide, and (3) whenever the optical signal of the fluorescent indicator indicating the quantity of the amplification product of the third target polynucleotide reaches or exceeds a predetermined level, reducing the polymerase extension time of the reaction to below the predetermined polymerase extension time but above each of the replication times of the first and second target polynucleotides, thereby terminating amplification of the third target polynucleotide.

2. The method of claim 1, wherein said amplification reaction is selected from the group consisting of a polymerase chain reaction (PCR), a nucleic acid sequence based amplification (NASBA), a ligase chain reaction (LCR), a strand displacement reaction (SDA), and a rolling circle amplification.

3. The method of claim 2, wherein said nucleic acid polymerase lacks strand displacement activity.

4. The method of claim 1, wherein amplification of the first target polynucleotide is terminated in the second stage reaction, further comprising:

monitoring the optical signals of the fluorescent indicators during the second stage reaction; and initiating a third stage reaction by changing the reaction condition of the second stage reaction as follows and in any order: whenever the optical signal of the fluorescent indicator indicating the quantity of the amplification product of the second target polynucleotide reaches or exceeds a predetermined level, increasing the primer annealing temperature of the reaction to above the predetermined primer annealing temperature but below the primer annealing temperatures of the third target polynucleotide, thereby terminating amplification of the second target polynucleotide, and whenever the optical signal of the fluorescent indicator indicating the quantity of the amplification product of the third target polynucleotide reaches or exceeds a predetermined level, reducing the polymerase extension time of the reaction to below the predetermined polymerase extension time but above the replication time of the second target polynucleotide, thereby terminating amplification of the third target polynucleotide.

5. The method of claim 1, wherein amplification of the second target polynucleotide is terminated in the second stage reaction, further comprising:

monitoring the optical signals of the fluorescent indicators during the second stage reaction; and initiating a third stage reaction by changing the reaction condition of the second stage reaction as follows and in any order: whenever the optical signal of the fluorescent indicator indicating the quantity of the amplification product of the first target polynucleotide reaches or exceeds a predetermined level, reducing the amplicon denaturation temperature of the reaction to below the predetermined amplicon melting temperature but above the amplicon melting temperature of the third target polynucleotide, thereby terminating amplification of the first target polynucleotide, and whenever the optical signal of the fluorescent indicator indicating the quantity of the amplification product of the third target polynucleotide reaches or exceeds a predetermined level, reducing the polymerase extension time of the reaction to below the predetermined polymerase extension time but above the replication time of the first target polynucleotide, thereby terminating amplification of the third target polynucleotide.

6. The method of claim 1, wherein amplification of the third target polynucleotide is terminated in the second stage reaction, further comprising:

monitoring the optical signals of the fluorescent indicators during the second stage reaction; and initiating a third stage reaction by changing the reaction condition of the second stage reaction as follows and in any order: whenever the optical signal of the fluorescent indicator indicating the quantity of the amplification product of the first target polynucleotide reaches or exceeds a predetermined level, reducing the amplicon denaturation temperature of the reaction to below the predetermined amplicon melting temperature but above the amplicon melting temperature of the second target polynucleotide, thereby terminating amplification of the first target polynucleotide, and whenever the optical signal of the fluorescent indicator indicating the quantity of the amplification product of the second target polynucleotide reaches or exceeds a predetermined level, increasing the primer annealing temperature of the reaction to above the predetermined primer annealing temperature but below the primer annealing temperature of the first target polynucleotide, thereby terminating amplification of the second target polynucleotide.

* * * * *